US010588579B2

(12) United States Patent
Sarkar et al.

(10) Patent No.: US 10,588,579 B2
(45) Date of Patent: Mar. 17, 2020

(54) METHOD AND SYSTEM FOR ONLINE NON-INTRUSIVE FATIGUE-STATE DETECTION IN A ROBOTIC CO-WORKING ENVIRONMENT

(71) Applicant: Tata Consultancy Services Limited, Mumbai (IN)

(72) Inventors: Chayan Sarkar, Kolkata (IN); Pradip Pramanick, Kolkata (IN)

(73) Assignee: Tata Consultancy Services Limited, Mumbai (IN)

(*) Notice: Subject to any disclaimer, the term of this patent is extended or adjusted under 35 U.S.C. 154(b) by 0 days.

(21) Appl. No.: 16/268,473

(22) Filed: Feb. 5, 2019

(65) Prior Publication Data
US 2020/0015761 A1    Jan. 16, 2020

(30) Foreign Application Priority Data

Jul. 10, 2018  (IN) .............................. 201821025682

(51) Int. Cl.
*A61B 5/11*  (2006.01)
*A61B 5/00*  (2006.01)
(Continued)

(52) U.S. Cl.
CPC ................ *A61B 5/746* (2013.01); *A61B 5/18* (2013.01); *A61B 5/227* (2013.01); *A61B 5/6887* (2013.01);
(Continued)

(58) Field of Classification Search
CPC ........... A61B 5/11; A61B 5/1118; A61B 5/18; A61B 5/227; A61B 5/6887; A61B 5/7246; A61B 5/746; G08B 21/02
See application file for complete search history.

(56) References Cited

U.S. PATENT DOCUMENTS

| 2004/0039426 A1* | 2/2004 | Hurtado | ................. A61N 1/321 607/48 |
| 2008/0001735 A1* | 1/2008 | Tran | .................... G06F 19/3418 340/539.22 |

(Continued)

FOREIGN PATENT DOCUMENTS

JP      2007/209453      8/2007

OTHER PUBLICATIONS

Li, P. et al. "A Smart Safety Helmet using IMU and EEG sensors for worker fatigue detection," *2014 IEEE International Symposium on Robotic and Sensors Environments (ROSE) Proceedings*, Oct. 16-18, 2014, Timisoara, Romania; 7 pages.

(Continued)

*Primary Examiner* — Andrew W Bee
(74) *Attorney, Agent, or Firm* — Finnegan, Henderson, Farabow, Garrett & Dunner LLP

(57) ABSTRACT

A method and a robotic system for online localized fatigue-state detection of a subject in a co-working environment using a non-intrusive approach is disclosed. A force sensor, mounted on the robotic system is capable of capturing effective force applied by local muscles of the subject co-working with the robotic system, providing a non-intrusive sensing. The captured force is analyzed on-line by the robotic system 102 to detect current fatigue state of the subject and proactively predict the future state of the subject. Thus, enables alerting the subject before time avoiding any possible accident.

7 Claims, 8 Drawing Sheets

(51) Int. Cl.
  *A61B 5/18* (2006.01)
  *A61B 5/22* (2006.01)
(52) U.S. Cl.
  CPC ........ *A61B 5/7246* (2013.01); *A61B 2503/12* (2013.01)

(56) References Cited

U.S. PATENT DOCUMENTS

| | | | |
|---|---|---|---|
| 2011/0251021 A1* | 10/2011 | Zavadsky | A63B 21/00 482/5 |
| 2015/0272501 A1* | 10/2015 | MacEachern | A61B 5/0531 600/301 |
| 2015/0283020 A1* | 10/2015 | Kim | A61B 5/11 623/24 |
| 2016/0262687 A1* | 9/2016 | Vaidyanathan | A61B 5/7264 |
| 2018/0289313 A1* | 10/2018 | Inan | A61B 5/4528 |
| 2018/0346256 A1* | 12/2018 | Kurihara | B65G 43/00 |
| 2019/0077007 A1* | 3/2019 | Mallinson | A61B 5/11 |

OTHER PUBLICATIONS

Al-Mulla, M.R. et al. (2011). "A Review of Non-Invasive Techniques to Detect and Predict Localised Muscle Fatigue," *Sensors*, vol. 11; pp. 3545-3594.

* cited by examiner

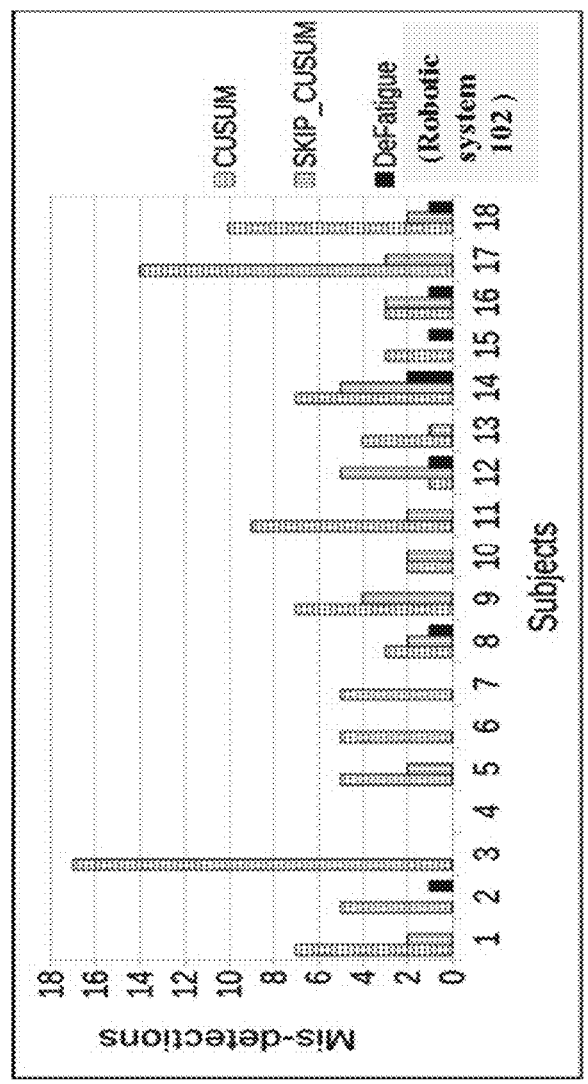
FIG. 3d CUSUM based detection v/s Robotic system 102

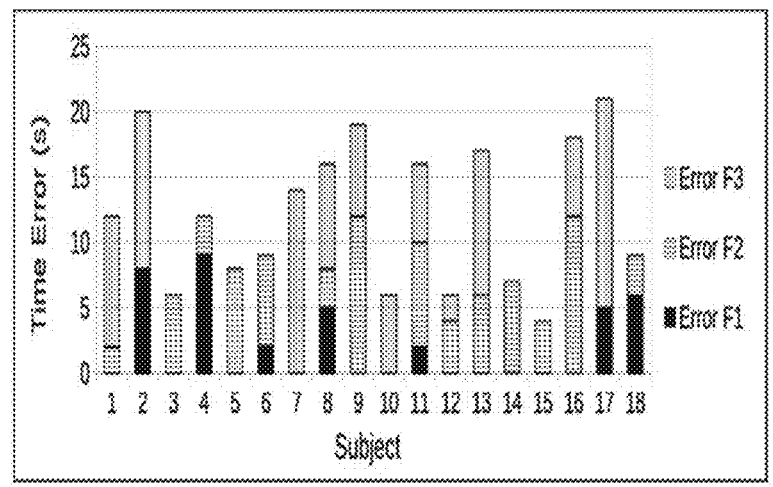
FIG. 3e
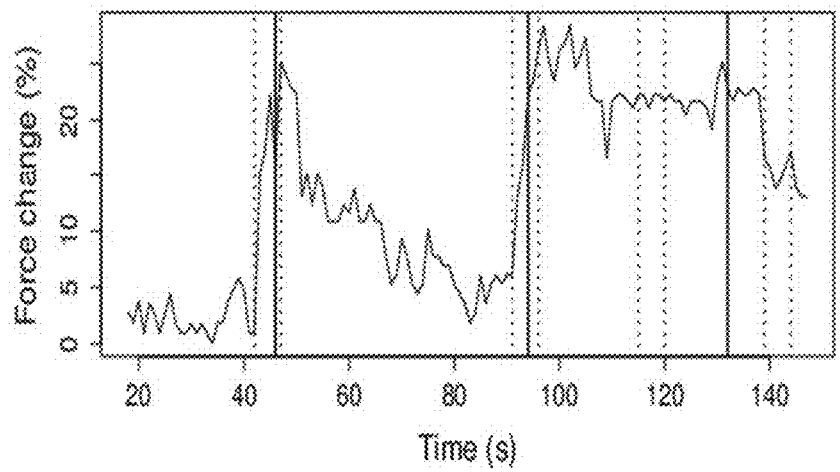
FIG. 3f Detected fatigue with false positive

METHOD AND SYSTEM FOR ONLINE NON-INTRUSIVE FATIGUE-STATE DETECTION IN A ROBOTIC CO-WORKING ENVIRONMENT

CROSS-REFERENCE TO RELATED APPLICATIONS AND PRIORITY

This application takes priority from the Indian filed application no. 201821025682 filed on 10 Jul. 2018 the entirety of which is hereby incorporated by reference.

DESCRIPTION

Technical Field

The disclosure herein generally relates to fatigue-state detection and, more particularly to fatigue-state detection in a robotic co-working environment.

Background

Robotic systems or robots have penetrated working environments, effectively reducing or eliminating manual intervention for task completions. However, with level of intelligence built in the robots, currently robots not only share the workplace between robots and humans, but also collaborate actively. Thus, it is frequent to see robots as a companion in daily surroundings for example, in domestic and commercial environments such as home, school, office, hospital, factory and the like. However, one of the major challenge for robots or robotic systems in being true cohabitants is the limited level of interaction between a robot and a subject. In scenarios of robotic co-working environment, where the robot and the subject work as a co-worker, implicit and timely interaction between the robot and the subject is very important. Especially, in the co-working environment where the subject and the robot together carry a heavy object, the collaboration is effective if the robot proactively can detect the instant when the subject is possibly to move into a fatigue state. The proactive action of the robot is critical to avoid any possible injury, which may sometimes prove fatal.

Some existing approaches provide solutions that can identify muscle fatigue, but they are intrusive requiring the subject to wear sensors. The intrusive techniques may not be a feasible and convenient approach in working environments such as environments where subject carry out physical work. In some other existing approaches video based non-intrusive techniques are utilized to identify overall fatigue state and specifically focus on drowsiness of the subject. However, in co-working environments with task such as lifting heavy loads, overall fatigue detection may not be the right approach for fatigue detection, rather effective approach is to detect the localized muscle fatigue for muscles in action. Thus, proactive detection of localized muscle fatigue is required to ensure safety and apply preventive measure to avoid undesired incidents.

SUMMARY

Embodiments of the present disclosure present technological improvements as solutions to one or more of the above-mentioned technical problems recognized by the inventors in conventional systems. For example, in one embodiment, a system, alternatively referred as a robotic system, for non-intrusive fatigue-state detection in a co-working environment is disclosed. The robotic system comprises a processor(s), an Input/Output (I/O) interface, a memory, wherein the memory comprises a sensor module associated with a sensor mounted on a robotic organ of the robotic system and a muscle fatigue detection module. The muscle fatigue detection module when executed by the processor(s) is configured to receive, from the sensor module, a signal corresponding to a force applied by a localized muscle of a subject, sensed by the sensor, while jointly performing a task with the robotic system in the co-working environment. Further, the muscle fatigue detection module is configured to detect transition of the received signal from a zero value to a non-zero value, wherein the non-zero value at the transition corresponds to a non-fatigue state of the subject. Further, the muscle fatigue detection module is configured to determine, on detection of the transition of the received signal to the non-zero value, a current fatigue state of the subject among a plurality of fatigue states. The current fatigue state is determined based on an initial average force $(F_I)$ associated with the non-fatigue state, wherein the plurality of fatigue states comprise the non-fatigue state, a plurality of intermediate fatigue states and a critical fatigue state. Further, the muscle fatigue detection module is configured to generate an alert for aborting the task if the current fatigue state is determined as the critical fatigue state.

In yet another embodiment, a method for non-intrusive fatigue-state detection in a co-working environment is disclosed. The method comprises receiving from a sensor module a signal corresponding to a force applied by a localized muscle of a subject, sensed by the sensor, while jointly performing a task with the robotic system in the co-working environment. Further, the method comprises detecting transition of the received signal from a zero value to a non-zero value, wherein the non-zero value at the transition corresponds to a non-fatigue state of the subject. Further, the method comprises determining, on detection of the transition of the received signal to the non-zero value, a current fatigue state of the subject among a plurality of fatigue states, wherein determination of the current fatigue state is based on an initial average force $(F_I)$ associated with the non-fatigue state, wherein the plurality of fatigue states comprise the non-fatigue state, a plurality of intermediate fatigue states and a critical fatigue state. Furthermore, the method comprises generating an alert for aborting the task if the current fatigue state is determined as the critical fatigue state.

In yet another embodiment, one or more non-transitory machine readable information storage mediums comprising one or more instructions which when executed by one or more hardware processors cause: receiving from a sensor module a signal corresponding to a force applied by a localized muscle of a subject, sensed by the sensor, while jointly performing a task with the robotic system in the co-working environment. Further, cause detecting transition of the received signal from a zero value to a non-zero value, wherein the non-zero value at the transition corresponds to a non-fatigue state of the subject. Further, cause determining, on detection of the transition of the received signal to the non-zero value, a current fatigue state of the subject among a plurality of fatigue states, wherein determination of the current fatigue state is based on an initial average force $(F_I)$ associated with the non-fatigue state, wherein the plurality of fatigue states comprise the non-fatigue state, a plurality of intermediate fatigue states and a critical fatigue state. Furthermore, cause generating an alert for aborting the task if the current fatigue state is determined as the critical fatigue state.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIGS. 3a-3f depict graphs for graphical analysis of various aspects of the system of FIG. 1 functionally described in FIG. 2, in accordance with some embodiments of the present disclosure.

DETAILED DESCRIPTION OF EMBODIMENTS

Figure 1:
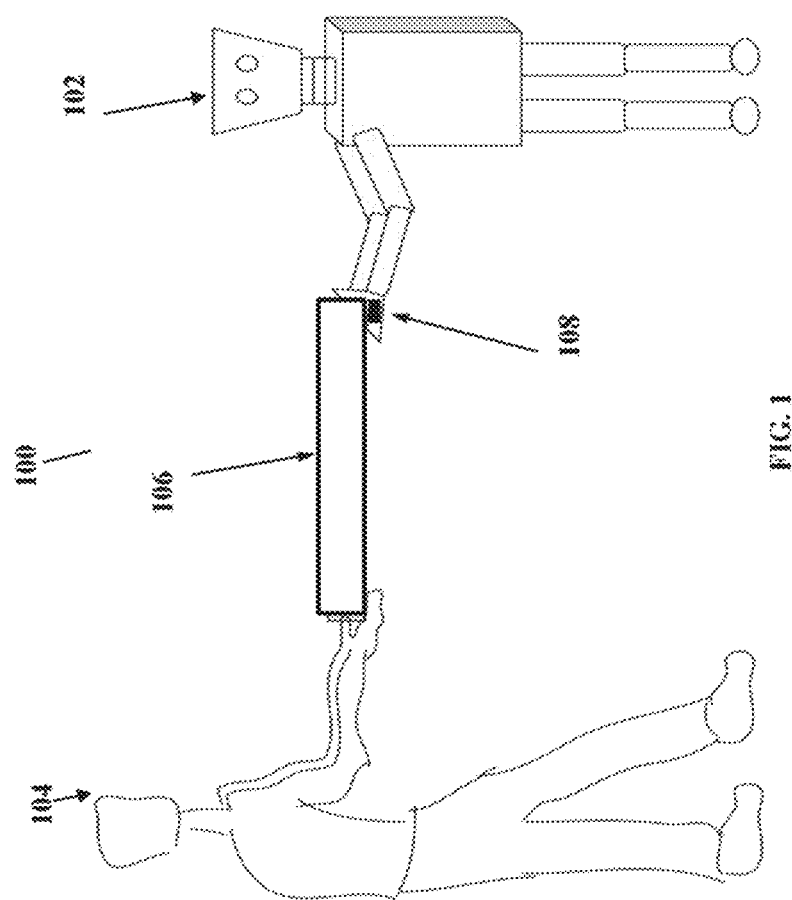
FIG. 1 illustrates an example robotic co-working environment implementing a system, alternatively referred as a robotic system, for online non-intrusive fatigue-state detection of a subject co-working with the system, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The embodiments herein provide a method and a system, interchangeably referred as robotic system, for online localized fatigue-state (fatigue state) detection of a subject in a co-working environment using a non-intrusive approach. The non-intrusive approach utilizes a force sensor(s) mounted on a robotic organ of the robotic system. The non-intrusive approach disclosed enables the subject to freely perform the task with no restriction on his/her natural movements, unlike intrusive conventional approaches. The force sensor(s) is mounted on the robotic organ, actively involved in performing the task jointly with the subject. The force sensor(s) senses and captures effective force applied by local muscles of the subject, wherein local muscles refer to one or more muscles of the subject that are directly or actively involved while performing the task, such as hand muscles involved while performing task of lifting heavy load. The force of the local muscles, so captured by sensor, is analyzed online by the robotic system, while the task is being performed. A current fatigue state of the local muscles of the subject is detected based on the on-line analysis performed. In tasks such as load lifting and the like, wherein local muscles are prominently in action, the localized muscle-fatigue detection is critical than overall fatigue detection. The disclosed method and system targets localized muscle-fatigue detection. In practical scenarios, decision about indicating a fatigue state is not a binary decision, especially for a muscle fatigue. Rather, muscle fatigue is a continuous accumulation of lactic acid while one or more muscles actively involved in the task actions are stressed. When two human beings collaborate, they often understand the fatigue state (may not be quantitatively) of the other person without explicit communication. A flag is generally raised when one person is completely unable to continue the work. Until then the work continues in cooperation between the co-workers. However, if one of the co-worker is a robot, it is essential to assess the fatigue state with every passing moment and decide whether to persist on the job (task) or not. The robotic system disclosed enables detecting fatigue state of any subject of unknown physical strength, which varies significantly from subject to subject. In order to be able to detect fatigue state of the subject, the system quantifies the muscle-fatigue states and the quantification is people agnostic. As known in the art, time to reach muscle fatigue generally depends upon several physiological properties of the subject such as age, height, weight, gender, physical wellness and the like, often cumulatively termed as physical strength. Moreover, there is also temporal variations of physical strength for the same subject (interchangeably referred as person), which makes the local muscle fatigue detection problem more challenging for existing methods. However, the disclosed system provides people agnostic approach as described in conjunction with FIGS. 1 to 4 below.

Referring now to the drawings, and more particularly to FIG. 1 through FIG. 4, where similar reference characters denote corresponding features consistently throughout the figures, there are shown preferred embodiments and these embodiments are described in the context of the following exemplary system and/or method.

FIG. 1 illustrates an example robotic co-working environment 100 implementing a system 102, alternatively referred as a robotic system, for online non-intrusive fatigue-state detection of a subject 104 co-working with the system 102, according to some embodiments of the present disclosure.

As depicted, in the example herein, the system 102 of humanoid robot, and the subject 104 jointly perform a task of lifting a load 106. A force sensor 108 (alternatively referred as sensor 108), placed on robot arm (organ of the humanoid robot or robotic system 102, senses the force applied by the subject 104 while lifting the load 106 (alternatively referred as object). The system 102 is configured to receive signals corresponding to the applied force from the force sensor 108. Further, the system 102 is configured to analyze the received signals to detect a current fatigue state of the subject and predict the future fatigue state. The system disclosed quantifies current fatigue state of any subject under observation into one among multiple fatigue states pre-defined by the robotic system 102. The multiple fatigue states include a non-fatigue state and three or more levels of fatigue state with increasing fatigue level. The subject 104 is monitored seamlessly to track variation in the current fatigue levels. The analysis of the variation of fatigue levels detected for the subject 104 are used to predict the possible future fatigue state. This, disclosed proactive approach enables the robotic system 102 to alert the subject 104 about his/her possible future fatigue state. If the future fatigue state is a state above a predefined fatigue threshold (also referred as critical fatigue state), the robotic system 102 may alert the subject indicating aborting of the task to prevent any possible accident. Thus, the proposed method and system enables detection of fatigue state the subject of any upcoming extreme fatigue state that may be harmful if attained, as the subject may possibly enter a breakdown state. Thus, disclosed system 102 ensures a safer co-working environment. Further, the disclosed system 102 is non-intrusive and user agnostic. Thus, it does not require any user-specific training or adaptation. Moreover, the detection is in real-time. Across all test cases, the disclosed system 102 shows very low mis-detections/over detections as compared to the state-of-the-art approaches. Moreover, the system 102 provides significantly less number of false negatives as compared to false positives.

An example force sensor 108, used for detecting the applied force by the subject 104 is described. The force sensor 108 comprises a robust polymer thick film (PTF) that exhibit a decrease in resistance with the increase of applied force. However, since the change in resistance is (very) small and not suitable for accurate measurement, a voltage divider is used to convert resistance output to voltage output, which has a larger scale. Thus, the voltage output of the force sensor 108 is increased with increasing force. The force sensor 108 acquires the signal (data) corresponding to the applied along with timestamps. Typical force sensor used is an FSR-402 that has sensitivity of 0.2N to 20 N. It has a circular sensing region with a diameter of 12 mm, which is suitable to be placed on the humanoid robot's hand (robotic organ to the robotic system 102). However, beyond the outer ring of the sensing region, there is a protective layer which prevents any object (load) larger than the sensing region to give accurate output. Also, the sensing region resides at a little lower height than the protective layer. So, for a rigid box with a flat base, which is larger than the sensor, the weight does not fall on the sensing region completely. A small, plastic, 3D-printed cylinder with a small base and large top is used to overcome this challenge. The manner in which the force sensor 108 is placed in the system 102, the weight of object or load 106 falls over the larger flat top of the cylinder. Even though the total weight of the box (load 106) is not reflected by the force sensor 108 output, the change in force on the force sensor 108 is measurable, and the system 102 utilizes this acquired data or signal.

Figure 2:
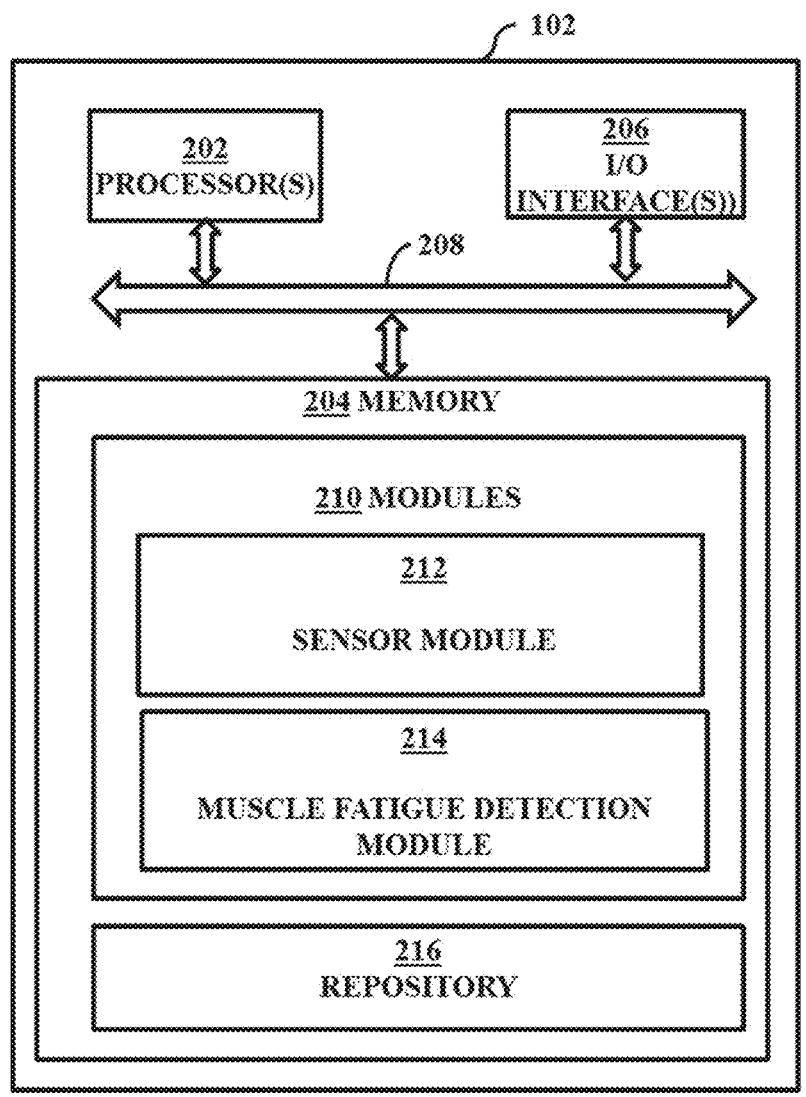
FIG. 2 illustrates a functional block diagram of the system of FIG. 1, according to some embodiments of the present disclosure.
Figure 4:
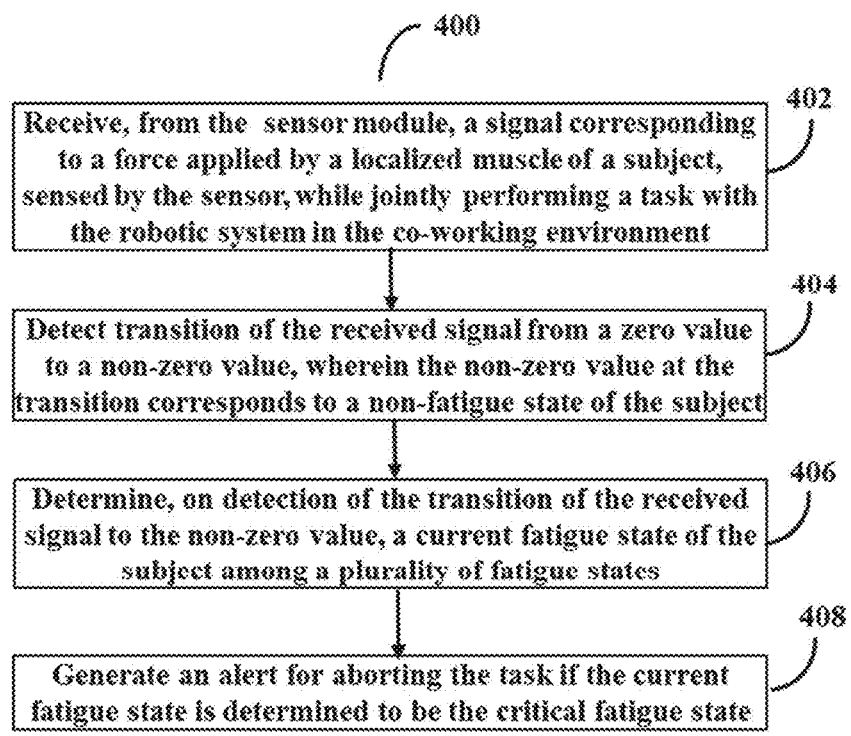
FIG. 4 is a flow diagram illustrating a method for online non-intrusive fatigue-state detection of the subject, in accordance with some embodiments of the present disclosure.

The system 102 is further explained in detail in conjunction with functional modules of FIG. 2 and flow diagram of FIG. 4 for localized muscle fatigue detection of the subject 104. In an embodiment, the system 102 can be any robotic system such as a humanoid robot, a robotic hand assembly and so on.

FIG. 2 illustrates a functional block diagram of the system 102 of FIG. 1, according to some embodiments of the present disclosure. The system 102 includes or is otherwise in communication with one or more hardware processors such as a processor(s) 202, at least one memory such as a memory 204, and an I/O interface 206. The processor 202 (hardware processor), the memory 204, and the I/O interface(s) 206 may be coupled by a system bus such as a system bus 208 or a similar mechanism. The memory 204 further may include modules 210. In an embodiment, the modules 210 include a sensor module 212, a muscle fatigue detection module 214 along with other modules (not shown), for implementing functions of the system 102. In an embodiment, the modules 210 can be an Integrated Circuit (IC) (not shown), external to the memory 204, implemented using a Field-Programmable Gate Array (FPGA) or an Application-Specific Integrated Circuit (ASIC). The names (or expressions or terms) of the modules of functional block within the modules 210 referred herein, are used for explanation and are not construed to be limitation(s). Further, the memory 204 can also include the repository 216. The data may be sensor data or sensor signals associated with a plurality signals monitored or acquired from the force sensor 108 attached to the subject(s) or the object (s) of interest, in one example embodiment. The force sensor data is then processed to identify the current muscle fatigue state of the subject 104.

Figure 3A:
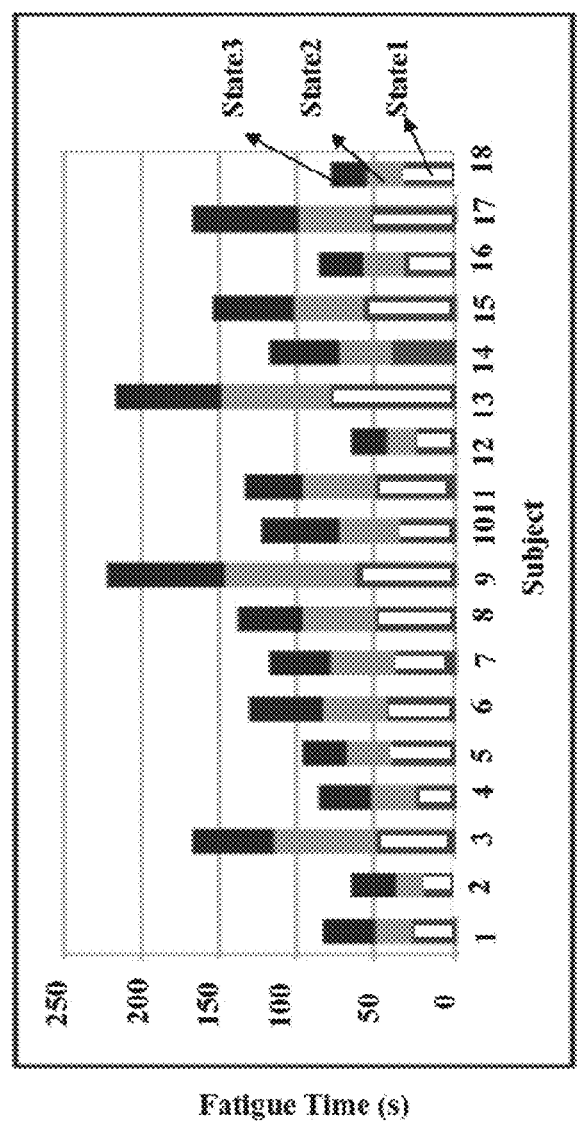

To determine the current muscle fatigue state of the subject 104, the muscle fatigue detection module 214 is configured to receive, from the sensor module, a signal corresponding to a force applied by a localized muscle of a subject while jointly performing a task with the robotic system 102 in the co-working environment 100. Further, the muscle fatigue detection module 214 is configured to determine the current fatigue state of the subject from among a plurality of fatigue states by analyzing the received signal. The analysis of the received signal is triggered when the received signal reflects a non-zero value. The plurality of fatigue states comprise an initial fatigue state, a plurality of intermediate fatigue states and a critical (or advanced) fatigue state. The plurality of fatigue states based on study carried out in the field may be as defined in table 1 below. FIG. 3a shows variations in time across the subject to reach the three fatigue states (state 1, state 2 and state 3). The plurality of fatigue states (state 1 through state 4) are example fatigue states considered to explain the disclosed system 102. However, the system 102 can be implemented for any number of fatigue levels that can be defined distinctly.

TABLE 1

| Muscle performance | Non-fatigue state | State1 (intermediate fatigue state) | State2 (intermediate fatigue state) | State 3 (critical fatigue state) | State 4 (extreme fatigue state) |
|---|---|---|---|---|---|
| Muscle discomfort | Ease and comfort in performing the task | tightness or slight cramping | continuous cramping with intermittent pain | continuous pain and desire to abandon | unable to sustain activity or task |
| Hand tremor increase | Steady hands | 138% | 225% | 300% | 350% |

Even though, there are four fatigue states in the table 1 above, the system 102 limits the detection of fatigue state to critical fatigue state (for example, state 3 for fatigue states considered in table 1 above). The logical reason being that any subject if reaches extreme fatigue state may meet an accident. Thus, to effectively detect and classify three states of fatigue (fatigue states) with very high accuracy, some assumptions are made based on the observations of data collection during experiments.

1. Let $F_I$ be the average force output of the sensor 108 during an initial time window $T_I$ due to the force applied by the subject 104 (a human being for the example explanation herein) while co-working with the robotic system 102. The muscle fatigue detection module 212 is configured to assume that during the initial time window $T_I$, the human being is in the non-fatigue state. Thus, FI reflects the force exerted by a hand muscle of the subject 104 during the non-fatigue state. To avoid the effect of noise and outliers, a robust statistic viz. median is used to calculate $F_I$. Let D be a set of n sensor samples collected in $T_I$ (a plurality of samples at regular sampling instants). Reordering D such that d1<d2<d3 ..., dn−1<dn, then $F_I$ is given by equation 1 below that applies a statistical median approach that averages current forces corresponding to each sample of the initial window to determine the initial average force associated with the non-fatigue state of the subject 104.

$$F_I = \begin{cases} d_{n+1/2}, & \text{when } n \text{ is odd} \\ \{d_{(n/2)} + d_{1+(\frac{n}{2})}\}/2, & \text{when } n \text{ is even} \end{cases} \quad (1a)$$

2. Let δT denote the time to reach the first fatigue state, which denotes the time difference between the start of the task and having the first state of fatigue. Then, the next state of fatigue is likely to occur after δT/2 time unit. This assumption is based on the fact that during the experiments, the next state of fatigue happens roughly in the following δT time unit, as shown in FIG. 3a but never before δT/2.

3. The transition from non-fatigue to fatigue state is not instantaneous, rather it happens during a short period of time. So a time window is required to analyze the trend of the sensor data of the sensor 108, which is received from the sensor module 212 for online detection of the fatigue state. Let $F_c$ be the current average force observed during time window $T_c$ (preset window interval). Then the normalized decrease in force from the initial average force ($F_I$) is denoted as in equation 2 below using a statistical mean approach:

$$'\delta F = (F_I - F_c)/F_I \cdot 100 \quad (1b)$$

4. In an embodiment, it is assumed that a normalized decrease in force by more than (δF>) 10% indicates a significant change; thus indicating the chance of "potential" fatigue. This δF is the cut-off threshold to find the window of interest in the force sensor data that is subject to further analysis. The value of δF is selected such that it reduce false positives. This threshold value is identified to be appropriate based on experiments, where all marked fatigue states from experimental dataset have more than 10% decrease in force. However, the threshold δF can be modified to trade off safety with accuracy.

Further, based on the mentioned assumptions, the steps followed by the muscle fatigue detection module 214 for online fatigue detection is as explained in conjunction with a method 400 of FIG. 4. Example method steps of the method start at the beginning of a human-robot collaborative task, which is triggered by a non-zero sensor reading. The example method terminates when the sensor reading is zero, indicating end/abortion of the task. The pseudo-code of the example method is described in the following:

Read $F_1$ using equation 1;
cut of f=10;
while (sensor reading>0) do (transition of received signal, from sensor 108, from a zero value to non-zero value)
  Select time windo $T_c$ (preset window interval);
  while (!$T_c$:full( )) do
    Fill $T_c$ with force sensor reading (moving window average);
  Calculate δF for time window $T_c$;
  if (δF>cut off) then
    Mark starting of potential fatigue; (mark the current time window as Window of Interest (WOI))
  Select time Window of Interest, $T_{WOI}$; (predefined time slot, for example, the experiment time slot of 5 seconds is used. Performance on varying time slots is shown in Table 2)
  While $T_{WOI}$ is not full, fill $T_{WOI}$ with δF;
  if Slope($T_{WOI}$)>0) then (check for slope of normalized decrease in force is positive
    Mark next fatigue state;
  Calculate δT;
  Wait for δT/2 time; (iterating the incrementing of the current fatigue state to next fatigue state after a hold period of half the (δT)
  Undo marked potential fatigue;

When the normalized force change (δF) is more than the cut-off threshold, a window of interest (WOI) opens up. The slope of the force data within this WOI determines whether a fatigue state transition has occurred or not. A decreasing trend in force during the WOI provides a clear indication of fatigue. If the data-points inside WOI is represented as a line, then a positive slope in the line denotes a decreasing trend in force. This is because WOI is filled with the normalized change δF, which becomes positive when force is decreasing. However, for example systems that implement the disclosed method 400 for localized muscle fatigue detection, such as embedded system like Arduino, the slope of the line is determined by a computationally simple method, described below.

Let $\delta F_1, \delta F_2 \ldots \delta F_n$ denote the data points in $T_{WOI}$;
Get the midpoint of $T_{WOI}$ as δFm Calculate $M_1$ as $M_1 = (\Sigma_{i=0}^{m-1} \delta F_i)/m$ Calculate $M_2$ as $M_2 = (\Sigma_{i=m}^{n} \delta F_i)/m$ Calculate $\delta M$ as $(M_2 - M_1)$;

return δM

Evaluation and Experimental Results

Figure 3B:
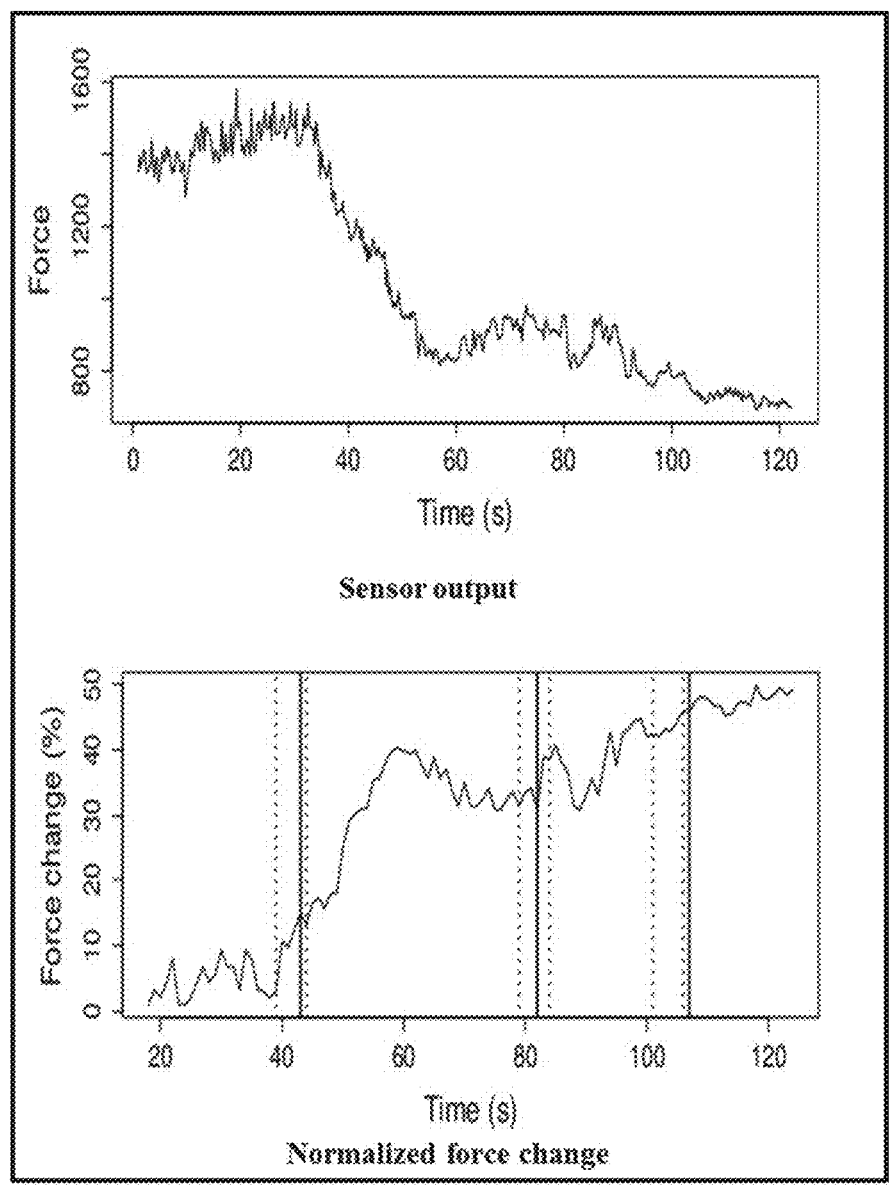

The system 102 disclosed herein detects the fatigue state transition on-the-go such that proactive measures can be taken in real-time. The accuracy of muscle fatigue detection along with timeliness is provided by the system 102. FIG. 3b shows a sample force sensor (sensor 108) output and the corresponding normalized change in force, respectively. FIG. 3b, depicting the corresponding normalized change in force also shows the detected fatigue states by the disclosed system 102 as indicated by a window of dashed lines. These lines denote the starting and ending points of WOI for which the potential fatigue is marked as positive. The vertical solid lines denote the ground truth provided by the subject. The FIG. 3b, depicting the corresponding normalized change in force, also depicts that the fatigue state transition is accurately indicated by system 102 as the ground truth falls within (or within close proximity of) the estimated window of transition. The summarized results for a plurality of the subjects on who were tested with the system 102 are provided in Table 2 below in terms of false positives and false negatives:

TABLE 2

| Subject | False positive | False negative |
| --- | --- | --- |
| 1 | 0 | 0 |
| 2 | 0 | 1 |
| 3 | 0 | 0 |
| 4 | 0 | 0 |

TABLE 2-continued

| Subject | False positive | False negative |
|---|---|---|
| 5 | 0 | 0 |
| 6 | 0 | 0 |
| 7 | 0 | 0 |
| 8 | 1 | 0 |
| 9 | 0 | 0 |
| 10 | 0 | 0 |
| 11 | 0 | 0 |
| 12 | 1 | 0 |
| 13 | 0 | 0 |
| 14 | 2 | 0 |
| 15 | 0 | 1 |
| 16 | 1 | 0 |
| 17 | 0 | 0 |
| 18 | 1 | 0 |

A false positive is marked when a WOI is given positive fatigue by the detection algorithm even though ground truth reported by the subject is not there. On the other hand, when the system misses a state transition, it is marked as false negative. To report the overall accuracy of the algorithm based on the data collected from the 18 subjects, following formula is utilized.

$$A = \{[S-(F_P+F_N)]/S\} \times 100\% \quad (2)$$

Where S, $F_P$, and $F_N$ are the total number of fatigue states, false positives, and false negatives, respectively. For 18 subjects, the total no. of fatigue states to be detected is 18×3=54. So the overall accuracy is $$A = \{[54-(6+2)]/54\} \times 100\% = 85.18\%$$

Figure 3C:
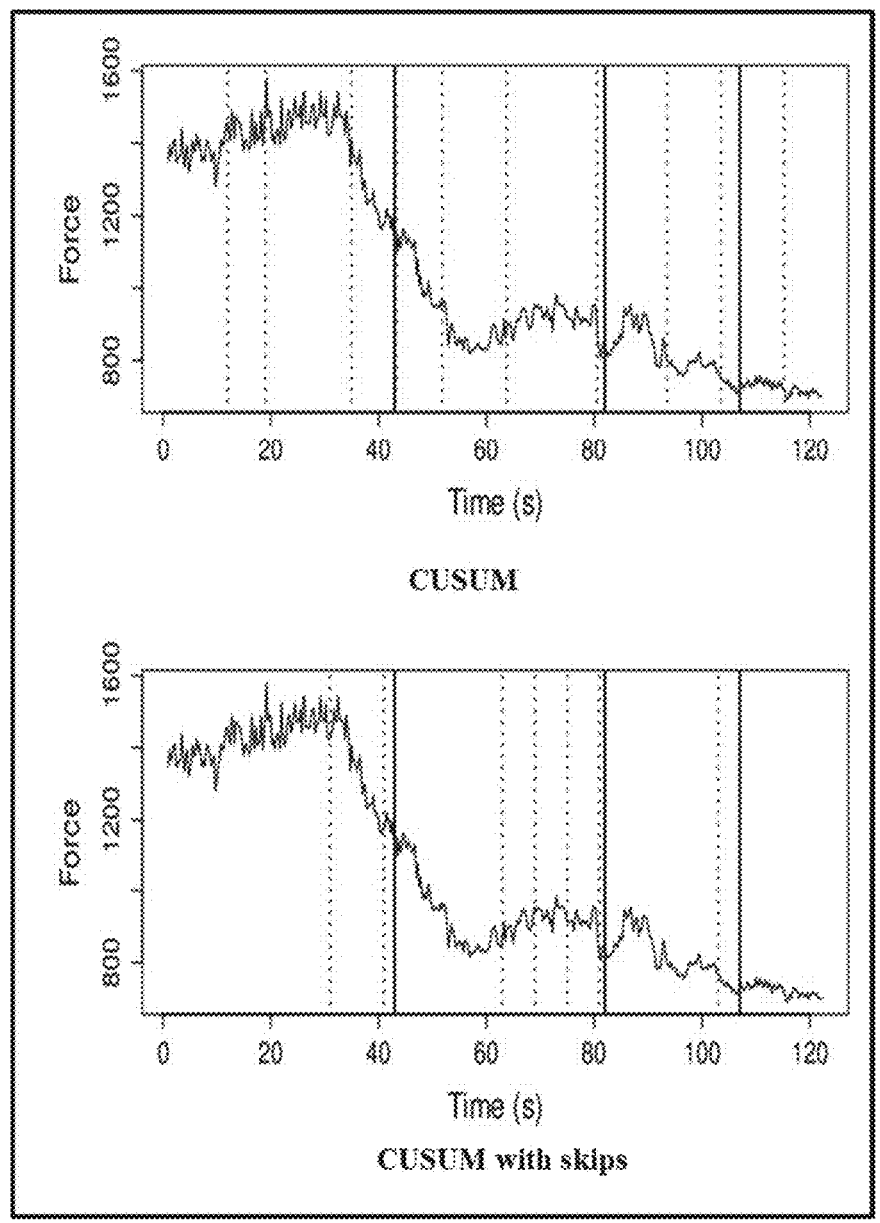

Further, the results of the system 102 are compared with the methodology described by existing approach that utilizes that uses cumulative sum control chart (CUSUM) to detect significant mean changes in the force sensor data. Even though the CUSUM actually works offline, for comparison herein, it is converted to detect changes online. The modified CUSUM change detection approach buffers data in a time window that is of the same size of the window used by the muscle fatigue detection module 214 of the system 102. It is identified that the CUSUM is very sensitive to perturbation and thus reports more false positives than the system 102, as depicted in FIG. 3*c* (CUSUM) for the same subject shown in FIG. 3*b*. The poor performance of CUSUM is attributed to the fact that it is not catered for noisy data. In case of driver's fatigue detection, hand grip force data contains lesser noise and there is high similarity among different subjects. Whereas in robot co-worker scenario, the sensor data incorporates noise from hand movements and varies significantly for different subjects. Fatigue not being an instantaneous event, there is a chance of falsely detecting the after-effects of a fatigue state transition as another state transition. As seen in FIG. 3*c* (CUSUM), the detected fatigue states by CUSUM are very close to each other and some of them are actually the after-effects of the previous fatigue state transition. As disclosed by the system 102, to avoid false positives of the after-effects, the system 102 waits for should wait for δT/2 time unit before checking for next fatigue state. Thus, system 102 introduces a waiting mechanism in CUSUM and it significantly reduces the rate of false positives. The modification in line with the system 102 is referred as SKIP CUSUM. A sample comparison of the same subject is shown in FIG. 3*c* (SKIP CUSUM). Detailed comparison of the three methods for all the 18 subjects is shown in FIG. 3*d*. Note that due to high sensitivity to mean change, both CUSUM and SKIP CUSUM reports zero false negative. However, CUSUM reports a large number of false positives. SKIP CUSUM performs better than CUSUM, but system 102 outperforms both in terms of accuracy per subjects. SKIP CUSUM reports a total of 33 false positives for the entire dataset, which results 38.89% accuracy using Eq. 2. With experiments conducted on the 18 subjects for the system 102, it was observed that fatigue being both physiological and psychological state, the subject may not report fatigue just as it happened. By visually analyzing the ground truth and the trend in force sensor data, it is found that sometimes the subjects reported fatigue a few seconds after it has actually happened. So the reported ground truth may not exactly fall inside the positive WOI of the system 102. However, sometimes it follows the window closely. So, apart from reporting accuracy in terms of the number of false positives and false negatives, also evaluated is accuracy w.r.t time difference between the ground truth and the positive WOI. The error of reporting fatigue by the system 102 is shown in FIG. 3*e*, where "Error F1" signifies the deviation of the detected window of first fatigue state from the ground truth, "Error F2" is for the second fatigue state, and so on. It can be seen that when the ground truth falls within the detected window, the deviation is zero; so the corresponding error is not shown in the FIG. 3*e*. Various parameters like the size of the initial time window ($T_I$), cut-off threshold, size of WOI and so on are selected.\ based on observations to maximize safety. These parameters are correlated with the nature of the task, like how long the task completion should take, what is the shape and weight of the jointly manipulated object and so on. However, it is assumed by collecting a little amount of data for a task, the robotic system 102 can learn about the correlation and hence adjust the thresholds dynamically. For the results shown in table 2, use a box weighting 20 kg is used and an initial time window is selected as 10 s, cut-off threshold 10%, and size of WOI as 5 s. The detection accuracy of the system 102 by varying parameters is shown in table 3 below:

TABLE 3

| Cut-off (%) | WOI(s) | False positive | False negative | Accuracy (%) |
|---|---|---|---|---|
| 6 | 2 | 12 | 1 | 77.8 |
| 8 | 5 | 8 | 2 | 81.5 |
| 10 | 5 | 6 | 2 | 85.3 |
| 12 | 5 | 7 | 3 | 81.5 |
| 10 | 3 | 12 | 2 | 74.1 |
| 10 | 7 | 9 | 2 | 79.1. |
| 10 | 9 | 8 | 2 | 81.5 |
| 10 | 12 | 6 | 3 | 83.3 |

As shown in table 3, increasing the cut-off threshold while keeping the size of WOI fixed, results in lesser number of false positive. This is because, with a larger cut-off threshold, the system 102 becomes lesser sensitive to force change. The system 102 detects a state transition only when there is a significantly larger change in force, which of course results from a fatigue state transition. However, with a larger cut-off threshold, the number of false negative also starts to increase. A larger cutoff means, there is a chance of missing out a fatigued state for physically stronger persons whose force change is lesser. Similarly, increasing the size of WOI reduces the number of false positives, as a larger WOI clearly captures the decreasing force trend. However, having a large WOI means the method disclosed has to wait for a long time before giving the alert, which is not desirable. Initially, by collecting data, the robotic system 102 can produce such a table as in table 3, and select the row which is optimal for the selected task. The more the robotic system 102 learns, more accurately it can fine-tune the parameters. However, merely selecting the row with the highest accuracy may not be suitable for this.

For safety considerations, a false negative is more undesirable than a false positive. So a row with the minimal weighted average of false positive and false negative is to be selected, where the weight of false negative is more and can be selected based on the safety requirements. In fact, the traditional concept of false positive may not be applicable here. The online approach of muscle fatigue detection disclosed herein is designed in such a way that any supposedly false positive with respect to the ground truth is really marked as an early warning. As seen in a sample detection plot in FIG. 3(e), there exists a false positive between the 2nd and the 3rd states of fatigue. However, the disclosed online approach marks the false positive window as the next fatigue next (3rd fatigue state in this case). By looking at the total data, it can be seen that marking of false positive leads to an early marking of the 3rd state of fatigue. Even though this reduces the productivity of the setup, it does not compromise the safety of the system. The time difference between the early-marked fatigue state and the ground truth is another measure of accuracy. Further, the system 102 is also evaluated based on this time deviation measure. It is to be noted that as the time to reach fatigue states varies for different subjects, the accuracy measured by time deviation must be normalized. For example, a smaller deviation may be critical for a subject with relatively quicker to reach fatigue, while the same deviation may not be critical for a subject with much larger time to reach fatigue. So to normalize, the accuracy is calculated using following formula for all the subjects and then take the average as the overall accuracy.

Let, $F_1$; $F_2$; $F_3$ denote the time to reach the first, second, and third fatigue states, respectively and $Et_1$; $Et_2$; $Et_3$ denote the respective time deviation by the system 102. Then timing accuracy for an individual subject is given by $$A'=\{[(F_1+F_2+F_3)-(Et_1+Et_2+Et_3)]/(F_1+F_2+F_3)\}\times 100\% \quad (3)$$

A table 4 below provides accuracy of the system 102 in terms of deviation (in seconds) of the detection window from the ground truth.

TABLE 4

| Subject | $Et_1 + Et_2 + Et_3$ | $F_1 + F_2 + F_3$ | Accuracy (%) |
|---|---|---|---|
| 1 | 12 | 82 | 85.4 |
| 2 | 20 | 63 | 68.3 |
| 3 | 6 | 166 | 96.4 |
| 4 | 12 | 86 | 86.1 |
| 5 | 8 | 96 | 91.7 |
| 6 | 9 | 129 | 93 |
| 7 | 14 | 115 | 88.6 |
| 8 | 16 | 138 | 88.4 |
| 9 | 19 | 221 | 91.4 |
| 10 | 6 | 121 | 95 |
| 11 | 16 | 133 | 87.9 |
| 12 | 6 | 63 | 90.1 |
| 13 | 17 | 216 | 92.1 |
| 14 | 7 | 117 | 94 |
| 15 | 4 | 153 | 97.3 |
| 16 | 18 | 86 | 79 |
| 17 | 21 | 167 | 87.4 |
| 18 | 10 | 76 | 86.8 |

Based on the accuracy in table 4, the average accuracy of all the subjects is calculated to be 88.83%.

FIG. 3f depicts detected fatigue with a false positive, where the fatigue detection is indicated by a window (marked by vertical dashed lines) and actual fatigue state transition (the ground truth) is indicated by vertical solid line.

As depicted in FIG. 2, the hardware processor(s) 202 may be implemented as one or more multicore processors, a microprocessors, microcomputers, microcontrollers, digital signal processors, central processing units, state machines, logic circuitries, and/or any devices that manipulate data based on operational instructions. Among other capabilities, the hardware processor 202 is configured to fetch and execute computer-readable instructions stored in the memory 204 and communicate with the modules 210, internal or external to the memory 204, for triggering execution of functions to be implemented by the modules 210.

The I/O interface(s) 206 in the system 102 may include a variety of software and hardware interfaces, for example, a web interface, a graphical user interface and the like. The interface(s) 206 may include a variety of software and hardware interfaces, for example, interfaces for peripheral device(s), such as a keyboard, a mouse, an external memory, sensor 108 and a display. The interface(s) 206 may enable the system 102 to communicate with other devices, web servers and external. The interface(s) 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interface(s) 206 may include one or more ports for connecting a number of computing systems with one another or to another server computer. The I/O interface(s) 206 may include one or more ports for connecting a number of devices to one another or to another server. The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. Further, the modules 210 may include routines, programs, objects, components, data structures, and so on, which perform particular tasks or implement particular abstract data types. The modules 210 may include computer-readable instructions that supplement applications or functions performed by the system 102. The repository 216 may store data that is processed, received, or generated as a result of the execution of one or more modules in the module(s) 210.

Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

FIG. 4 is a flow diagram illustrating the method 400 for online non-intrusive fatigue-state detection of the subject 104 co-working with the system 102, in accordance with some embodiments of the present disclosure.

In an embodiment, the system 102, alternatively referred as the robotic system 102, includes one or more data storage devices or memory 204 (comprising the muscle fatigue detection module 214) operatively coupled to the one or more processors 202 and is configured to store instructions configured for execution of steps of the method 400 by the one or more processors 202. The steps of the method 200 are explained with reference to the components of the system 100 of FIG. 1. The method 400 can be further understood in conjunction with the description for system 102, as provided in FIG. 2, and not repeated for brevity. In an embodiment, at step 402, the method 400 includes enabling the muscle fatigue detection module 214 to receive, from the sensor module the signal corresponding to the force applied by the localized muscle of the subject (104). The force signal is sensed by the sensor 108 while the subject 104 jointly performing the task with the robotic system (102) in the co-working environment 100. At step 404, the method 400 includes enabling the muscle fatigue detection 214 to detect transition of the received signal from the zero value to the non-zero value. The wherein the non-zero value at the transition corresponds to the non-fatigue state of the subject (104). Upon detection of the transition of the received signal to the non-zero value, at step 406, the method 400 includes enabling the muscle fatigue detection 214 to determine the current fatigue state of the subject (104) among the plurality of fatigue states. The determination of the current fatigue state is based on the initial average force ($F_I$) associated with the non-fatigue. The plurality of fatigue states comprise the non-fatigue state, the plurality of intermediate fatigue states and the critical fatigue state as in table 1. At step 408, the method 400 includes enabling the muscle fatigue detection 214 to generate alert for aborting the task if the current fatigue state is determined as the critical fatigue state.

Determining the current fatigue state, at step 406, comprises windowing the received signal with a window of a preset window interval (Tc) to select the initial window as the current window. The preset window interval, interchangeably referred as window interval, for the initial window starts from origin of the received signal. Further, the determining comprises sampling the initial window into the plurality of samples at regular sampling instants. Each sample from the plurality of samples corresponds to the current force applied by the subject at the corresponding sampling instant from the sampling instants. Further, the method 400 comprises applying the statistical median approach as in equation 1 a that averages current forces corresponding to each sample of the initial window to determine the initial average force ($F_I$) associated with the non-fatigue state of the subject (104). The current fatigue state is marked as the initial fatigue state during analysis of the initial window. Further, the method 400 comprises sliding the window over the received signal by the predefined sliding interval to select a successive window next to the initial window, wherein post sliding, the successive window is the current window. The method 400 further comprises determining the current average force ($F_c$) for the successive window based on the statistical mean approach that averages current forces corresponding to each sample of the successive window. The method further comprises computing the normalized decrease in force ($\delta F$) of the subject based on the current average force and the initial average force. Further, the method 400 comprises detecting whether the normalized decrease in force ($\delta F$) is above the predefined force threshold. For example 10% as explained in FIG. 2. Further, the method comprises marking the current window as the WOI if the normalized decrease in force is above the predefined force threshold and repeating computation of normalized decrease in force for the predefined time slot ($T_{WOI}$) for the plurality of successive windows selected after the WOI. Further, the method 400 comprises determining whether slope of normalized decrease in force computed for the plurality of successive windows for the predefined time slot, is positive and incrementing the current fatigue state from the non-fatigue state to the next fatigue state among the plurality of fatigue states. The current state is indicated to the subject, letting him be aware of the muscle fatigue he/she is approaching. Further, the method 400 comprises determining a time interval ($\delta T$) between the non-fatigue state to next intermediate fatigue state and iterating the incrementing of the current fatigue state to next fatigue state after the hold period of half the ($\delta T$). The iteration continues till the current fatigue state reaches the critical fatigue state. Further, the method 400 comprises generating the alert for aborting the task when the current fatigue state reaches the critical fatigue state.

The illustrated steps of method 400 are set out to explain the exemplary embodiments shown, and it should be anticipated that ongoing technological development may change the manner in which particular functions are performed. These examples are presented herein for purposes of illustration, and not limitation.

The method 400 disclosed herein provides online detection, simplicity, adaptiveness and robustness with non-intrusive approach. The online detection: Practically, any fatigue detection system, such as the system 102, cannot wait for a stream of future data from the sensor to establish the current fatigue state. Even though analyzing the whole time-series data may accurately classify the fatigue state change in the time domain, it might be too late to avert the possibility of accident. Thus, required is to provide timely detection of the fatigue state such that proactive actions can be taken to avoid any accident. The online detection, as disclosed, is a necessity. Further, the system 102 provides a simple to implement solution with a simple detection logic running on the system 102 for a system mounted force sensor enabling detecting the current fatigue state in a time-bounded manner with the sensor data processing performed locally. Thus, system 102 can be a low-cost robotic system, still providing output in semi-real-time. Any computationally complex approach needs to be offloaded to run on a server, thus reliability of such approaches may decrease due to network latency and disconnection, unlike the onboard computation approach of the system 102 that provides online and real time processing for localized muscle fatigue detection. The system 102 is adaptive and robust to handle significant variation of physical strength among different persons. Moreover, the system 102 does not assume that the human worker (subject) would always hold the object in a certain way. Rather, it is agnostic to the holding pattern of an individual and the associated noise induced due to the holding pattern. Instead of customizing the logic for each person, the method and system disclosed is adaptive for any human co-worker, irrespective of her physical strength, holding pattern and so on. The system 102 is non-intrusive. Further, since the disclosed system 102 is people agnostic, it provides an advantage that if one co-worker is fatigued and other replaces him/her, the system does not require to reset any parameter for the change in the subject but can continue monitoring fatigue for the new subject. Unlike intrusive approach, where a replaced coworker will need to wear the sensor prior to replacing the fatigued worker for the task, which are not be feasible and convenient, the disclosed method and system is easy to use.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A robotic system for non-intrusive fatigue-state detection in a co-working environment, wherein the robotic system comprises:
   one or more processors;
   an Input/Output (I/O) interface;
   a memory, the memory storing instructions that, when executed by the one or more processors, configured the one or more processors to:
   receive, from a sensor mounted on a robotic organ of the robotic system, a signal corresponding to a force applied by a localized muscle of a subject, sensed by the sensor, while jointly performing a task with the robotic system in the co-working environment;
   detect transition of the received signal from a zero value to a non-zero value, wherein the non-zero value at the transition corresponds to a non-fatigue state of the subject;
   determine, on detection of the transition of the received signal to the non-zero value, a current fatigue state of the subject among a plurality of fatigue states, wherein the current fatigue state is determined based on an initial average force ($F_I$) associated with the non-fatigue state, wherein the plurality of fatigue states comprise the non-fatigue state, a plurality of intermediate fatigue states and a critical fatigue state; and
   generate an alert for aborting the task if the current fatigue state is determined as the critical fatigue state.

2. The robotic system of claim 1, wherein the one or more processors are configured to determine the current fatigue state by:
   windowing the received signal with a window of a preset window interval (Tc) to select an initial window as a current window, wherein the preset window interval for the initial window starts from an origin of the received signal;
   sampling the initial window into a plurality of samples at regular sampling instants, wherein each sample from the plurality of samples corresponds to a current force applied by the subject at a corresponding sampling instant from the sampling instants;
   applying a statistical median approach on a current force corresponding to each sample of the initial window to determine the initial average force ($F_I$) associated with the non-fatigue state of the subject, wherein the current fatigue state is marked as the initial fatigue state during analysis of the initial window;
   sliding the window over the received signal by a predefined sliding interval to select a successive window next to the initial window, wherein, after sliding, the successive window is the current window;
   determining a current average force ($F_c$) for the successive window based on a statistical mean approach that averages current forces corresponding to each sample of the successive window; and computing a normalized decrease in force (δF) of the subject based on the current average force and the initial average force.

3. The robotic system of claim 2, wherein the one or more processors are further configured to determine the current fatigue state by:
   detecting whether the normalized decrease in force (δF) is above a predefined force threshold;
   marking the current window as a Window of Interest (WOI) if the normalized decrease in force is above the predefined force threshold;
   repeating computation of normalized decrease in force for a predefined time slot ($T_{WOI}$) for a plurality of successive windows selected after the WOI;
   determining whether a slope of the normalized decrease in force computed for the plurality of successive windows for the predefined time slot is positive;
   incrementing the current fatigue state from the non-fatigue state to a next fatigue state among the plurality of fatigue states and indicate the current fatigue state to the subject;
   determining a time interval (δT) between the non-fatigue state to next intermediate fatigue states;
   iterating the incrementing of the current fatigue state to next fatigue state after a hold period of half the time interval (δT), wherein iteration continues till the current fatigue state reaches the critical fatigue state; and
   generating the alert for aborting the task when the current fatigue state reaches the critical fatigue state.

4. A method for non-intrusive fatigue-state detection in a co-working environment, wherein the method comprises:
   receiving, from a sensor, a signal corresponding to a force applied by a localized muscle of a subject, sensed by the sensor, while jointly performing a task with a robotic system in the co-working environment;
   detecting transition of the received signal from a zero value to a non-zero value, wherein the non-zero value at the transition corresponds to a non-fatigue state of the subject;
   determining on detection of the transition of the received signal to the non-zero value, a current fatigue state of the subject among a plurality of fatigue states, wherein the current fatigue state is determined based on an initial average force ($F_I$) associated with the non-fatigue state, wherein the plurality of fatigue states comprise the non-fatigue state, a plurality of intermediate fatigue states and a critical fatigue state; and
   generating an alert for aborting the task if the current fatigue state is determined as the critical fatigue state.

5. The method of claim 4, wherein determining the current fatigue state comprises:
   windowing the received signal with a window of a preset window interval (Tc) to select an initial window as a current window, wherein the preset window interval for the initial window starts from an origin of the received signal;
   sampling the initial window into a plurality of samples at regular sampling instants, wherein each sample from the plurality of samples corresponds to a current force applied by the subject at a corresponding sampling instant from the sampling instants;
   applying a statistical median approach on current forces corresponding to each sample of the initial window to determine the initial average force ($F_I$) associated with the non-fatigue state of the subject, wherein the current fatigue state is marked as the initial fatigue state during analysis of the initial window;
   sliding the window over the received signal by a predefined sliding interval to select a successive window next to the initial window, wherein, after sliding, the successive window is the current window;
   determining a current average force ($F_c$) for the successive window based on a statistical mean approach that averages current forces corresponding to each sample of the successive window; and
   computing a normalized decrease in force (δF) of the subject based on the current average force and the initial average force.

6. The method of claim 5, wherein determining the current fatigue state further comprises:
   detecting whether the normalized decrease in force (δF) is above a predefined force threshold;
   marking the current window as a Window of Interest (WOI) if the normalized decrease in force is above the predefined force threshold;
   repeating computation of normalized decrease in force for a predefined time slot ($T_{WOI}$) for a plurality of successive windows selected after the WOI;
   determining whether a slope of the normalized decrease in force computed for the plurality of successive windows for the predefined time slot, is positive;
   incrementing the current fatigue state from the non-fatigue state to a next fatigue state among the plurality of fatigue states and indicate the current fatigue state to the subject;
   determining a time interval (δT) between the non-fatigue state to next intermediate fatigue states;
   iterating the incrementing of the current fatigue state to next fatigue state after a hold period of half the time interval (δT), wherein iteration continues till the current fatigue state reaches the critical fatigue state; and
   generating the alert for aborting the task when the current fatigue state reaches the critical fatigue state.

7. One or more non-transitory machine readable information storage media storing instructions which when executed by one or more hardware processors cause the one or more hardware processors to perform a method comprising:
   receiving a signal corresponding to a force applied by a localized muscle of a subject, sensed by a sensor, while jointly performing a task with a robotic system in a co-working environment;
   detecting transition of the received signal from a zero value to a non-zero value, wherein the non-zero value at the transition corresponds to a non-fatigue state of the subject;
   determining on detection of the transition of the received signal to the non-zero value, a current fatigue state of the subject among a plurality of fatigue states, wherein the current fatigue state is determined based on an initial average force ($F_I$) associated with the non-fatigue state, wherein the plurality of fatigue states comprise the non-fatigue state, a plurality of intermediate fatigue states and a critical fatigue state; and
   generating an alert for aborting the task if the current fatigue state is determined as the critical fatigue state.

\* \* \* \* \*